United States Patent [19]

Ishikawa

[11] Patent Number: 5,480,394
[45] Date of Patent: Jan. 2, 1996

[54] FLEXIBLE MEMBER FOR USE AS A MEDICAL BAG

[75] Inventor: Kenji Ishikawa, Kanagawa, Japan

[73] Assignee: Terumo Kabushiki Kaisha, Tokyo, Japan

[21] Appl. No.: 66,015

[22] PCT Filed: Jun. 11, 1992

[86] PCT No.: PCT/JP92/00749

§ 371 Date: May 27, 1993

§ 102(e) Date: May 27, 1993

[87] PCT Pub. No.: WO93/05824

PCT Pub. Date: Apr. 1, 1993

[30] Foreign Application Priority Data

Sep. 27, 1991 [JP] Japan ................................. 3-249446
Nov. 14, 1991 [JP] Japan ................................. 3-298959

[51] Int. Cl.$^6$ ................................................. A61M 1/00
[52] U.S. Cl. ........................ 604/327; 604/403; 604/408; 383/1
[58] Field of Search ............................ 604/327, 339, 604/349, 355, 356, 403, 408, 409, 410; 383/1

[56] References Cited

U.S. PATENT DOCUMENTS 4,438,253  3/1984  Casey et al. .
4,876,311  10/1989  Hennig et al. .
5,158,810  10/1992  Oishi et al. ............................ 604/408
5,195,987  3/1993  Karpiak .................................. 604/408
5,226,564  7/1993  Steer et al. ............................. 604/408

FOREIGN PATENT DOCUMENTS 0288908  11/1988  European Pat. Off. .
2209918  8/1990  Japan .
3187386  8/1991  Japan .
4136066  5/1992  Japan .
4136067  5/1992  Japan .

Primary Examiner—C. Fred Rosenbaum
Assistant Examiner—Ronald K. Stright, Jr.
Attorney, Agent, or Firm—Burns, Doane, Swecker & Mathis

[57] ABSTRACT

According to the present invention, there is provided a highly biodegradable flexible member adapted for medical use which is capable of undergoing degradation in a relatively short period of time in natural environment by burying in soil or abandoning in sea after its sterilization so that no environmental pollution would be caused by its disposal, and which additionally has excellent workability, cost performance, compatibility to ecosystem, as well as biocompatibility. At least a portion of the flexible medical member is fabricated from a material containing a resin composition comprising a polyhydroxyalkanoate, a copolymer thereof, or a mixture thereof as its main component, and 0.01 to 60% by weight of a lipid compound.

7 Claims, 4 Drawing Sheets

FLEXIBLE MEMBER FOR USE AS A MEDICAL BAG

TECHNICAL FIELD

This invention relates to a flexible member for medical use having biodegradability as well as excellent physical properties including flexibility, impact resistance and workability.

BACKGROUND ART

Conventional flexible materials which have been used for medical purposes include materials mainly comprising polyvinyl chloride having blended therein a plasticizing agent selected from phthalic acid-based compounds such as dioctyl phthalate and 2-ethylhexyl phthalate in an amount of from 10 to 100% by weight per 100% by weight of the polyvinyl chloride; materials mainly comprising an elastomer resin such as a styrene-butadiene-styrene-based resin, for example an ABA-type block copolymer, an ethylene-propylene copolymer, a polyester elastomer or a polyurethane elastomer; and flexible resins such as an ethylene-vinyl acetate copolymer and an ethylene-ethylacrylate copolymer.

Most of the flexible medical members fabricated from such materials, for example, blood bags, tubes, catheters and the like, are disposable products, and after their use, they are abandoned as waste materials. These materials, however, do not undergo environmental degradation and retain their original shape for a prolonged period of time. It is well known that such waste materials have induced various social problems including the pollution.

In order to solve such problems, various investigations have been recently carried forward to develop biodegradable materials, namely, high molecular weight materials capable of being decomposed in ecosystem when placed or abandoned in the environment, and these materials have attracted a considerable public attention.

Of the conventionally known high molecular weight biodegradable materials, those comprising polypropylene, polyethylene or the like having blended therein corn starch for the purpose of their morphological collapse can not be deemed essentially biodegradable, since these materials only experience morphological change with the lapse of time, and the high molecular weight backbone of the polypropylene or polyethylene do not undergo any degradation.

Another group of biodegradable materials known in the art are poly(3-hydroxybutyrate) and copolymers mainly comprising the poly(3-hydroxybutyrate). Poly(3-hydroxybutyrate) is a material which has been confirmed to undergo a considerable environmental degradation, and to have an excellent biocompatibility. Therefore, this material was highly expected to have various applications in medical and other fields.

Contrary to such expectations, the poly(3-hydroxybutyrate) failed to find a large number of applications due to insufficiency in its impact resistance and other physical properties because of its hardness and brittleness. The poly(3-hydroxybutyrate) is also poor in its workability since it undergoes decomposition in the vicinity of its melting point in spite of its useful thermoplasticity.

In view of such conditions, various attempts have been made to modify the physical properties of the poly(3-hydroxybutyrate). Japanese Patent Application Kokai No. 63(1988)-269989 discloses a copolymer comprising recurring structural units of D-(−)3-hydroxybutyrate and D-(−)3-hydroxyvalerate. This material has attained considerable improvements in reducing melting point and in increasing flexibility. Synthesis of this material, however, could be effected only at a low productivity, and also, required a special substrate for the fermentation. As a consequence, this copolymeric material was rather expensive to detract from its availability as a general-purpose material.

Other attempts of altering the physical properties of the poly(3-hydroxybutyrate) include modification of the poly(3-hydroxybutyrate) by mixing with such resin materials as polyethylene oxide, ethylene propylene rubber, and polyvinyl acetate. None of the attempts, however, have fully succeeded in providing the stability, cost performance, workability, and the like with the resulting resin compositions. Use of such resin compositions for medical applications would be even more difficult since such applications would further require high safety and hygienic properties.

SUMMARY OF THE INVENTION

An object of the present invention is to obviate the above-described problems of the prior art by using a predetermined resin composition as a material for fabricating the flexible medical member, and thereby provide a highly biodegradable flexible member for medical use which is capable of undergoing degradation in a relatively short period of time in natural environment by burying in soil or abandoning in sea after its sterilization so that no environmental pollution would be caused by its disposal, and which additionally has excellent biocompatibility, compatibility to ecosystem, workability as well as cost performance.

Such an object is achieved by the present invention as described below.

According to the present invention, there is provided a flexible member for medical use which is characterized in that at least a portion of the member is prepared from a material containing a resin composition comprising a polyhydroxyalkanoate, a copolymer thereof, or a mixture thereof as its main component, and 0.01 to 60% by weight of a lipid compound.

The polyhydroxyalkanoate may preferably be at least a member selected from poly(3-hydroxyalkanoate)s, poly(4-hydroxyalkanoate)s, and poly(5-hydroxyalkanoate)s.

It is preferable that the flexible medical member has a tubular configuration to constitute at least a part of a member, for example, an infusion system, a blood transfusion system, a blood circulation circuit, or a catheter.

It is also preferable that the flexible medical member is a member in the form of a bag, for example, a blood bag, an infusion bag, a dialysis bag, or a perintestinal nutrient bag.

Furthermore, it is preferable that the flexible medical member is a member in the form of a thread, a woven fabric, or a nonwoven fabric, for example, a suture, a mesh, a patch, a pledget, and a prosthesis.

Still further, it is preferable that the flexible medical member is a member selected from a staple, a clip and a coalescence-preventing membrane.

BEST MODE FOR CARRYING OUT THE INVENTION

The flexible member for medical use according to the present invention is hereinafter described in further detail.

The flexible member for medical use of the present invention is a member wherein at least a part of the member comprises a resin composition basically comprising a polyhydroxyalkanoate, a copolymer thereof, or a mixture thereof, and further comprising from 0.01 to 60% by weight of a lipid compound; a complex material comprising a mixture of such a resin composition with another resin; or a processed material comprising such as a resin composition and another resin material. Such a flexible member for medical use of the present invention is suitable for various medical members including those which have been conventionally fabricated from the above-mentioned flexible material comprising polyvinyl chloride having added thereto dioctyl phthalate, for example, a blood bag, an infusion bag, a dialysis bag, a perintestinal nutrient bag, and the like, and various tubings and manifolds to be connected to such bags, as well as catheters, and the like; those fabricated from thread-like products, and woven and nonwoven fabrics, for example, a suture, a mesh, a patch, a pledget, a prosthesis, and the like; and those requiring non-brittleness as well as flexibility, for example, a staple and a clip. Among these, the flexible medical member of the present invention is particularly suitable for a disposable medical member.

Such a flexible member for medical use of the present invention is inexpensive, and has sufficient productivity, flexibility, corrosion resistance, workability, cost performance, compatibility to ecosystem, biocompatibility, as well as excellent biodegradability to cause no environmental pollution after its disposal.

The flexible member for medical use of the present invention basically comprises a highly biodegradable resin composition comprising a polyhydroxyalkanoate, a copolymer thereof, or a mixture thereof as its main component, and 0.01 to 60% by weight of a lipid compound.

The polyhydroxyalkanoates which may be used in the present invention include those comprising recurring units of a hydroxyalkanoate having about 3 to 12 carbon atoms. Preferable examples of the polyhydroxyalkanoate include poly(3-hydroxyalkanoate)s such as poly(3-hydroxypropionate), poly(3-hydroxybutyrate), poly(3-hydroxyvalerate), poly(3-hydroxyoctanoate), etc; poly(4-hydroxyalkanoate)s such as poly(4-hydroxybutyrate), poly(4-hydroxyvalerate), etc; and poly(5-hydroxyalkanoate)s such as poly(5-hydroxyvalerate), etc.

Among these, poly(3-hydroxybutyrate) may most preferably be used in the present invention.

In the present invention, not only the use of homopolymers of the hydroxyalkanoate, but also the use of copolymers of the hydroxyalkanoates are preferable.

Exemplary copolymers of the hydroxyalkanoates include copolymers of 3-hydroxybutyrate with another hydroxyalkanoate having 3 to 12 carbon atoms. Non-limiting preferable examples include (3-hydroxybutyrate)-(3-hydroxypropionate) copolymer, (3-hydroxybutyrate)-(3-hydroxypropionate)-(4-hydroxybutyrate) copolymer, (3-hydroxybutyrate)-(3-hydroxyvalerate) copolymer, (3-hydroxybutyrate)-(3-hydroxyvalerate)-(3-hydroxyhexanoate)-(3-hydroxyheptanoate)-copolymer, (3-hydroxybutyrate)-(3-hydroxyvalerate)-(3-hydroxyhexanoate)-(3-hydroxyheptanoate)-(3-hydroxyoctanoate) copolymer, (3-hydroxybutyrate)-(3-hydroxyhexanoate)-(3-hydroxyoctanoate) copolymer, (3-hydroxyoctanoate)-(3-hydroxylaurate) copolymer, (3-hydroxybutyrate)-(4-hydroxydibutyrate) copolymer, (3-hydroxybutyrate)-(4-hydroxyvalerate) copolymer, and (3-hydroxybutyrate)-(5-hydroxyvalerate) copolymer.

In the present invention, use of a mixture of the above-mentioned polyhydroxyalkanoates, a mixture of the above-mentioned copolymers, as well as a mixture of the above-mentioned polyhydroxyalkanoate and the above-mentioned copolymer are also preferred.

As is well known in the art, the polyhydroxyalkanoates and their copolymers are produced by various microorganisms. Those produced by any microorganism may be employed in the present invention.

Chemically synthesized polyhydroxyalkanoates and copolymers thereof may also be used in the present invention.

The microorganisms which produce a polyhydroxyalkanoate include, for example, various species of bacteria belonging to Acinetobacter, Actinomycetes, Alcaligenes, Aphanothese, Aquaspirillum, Azospirillum, Azotobacter, Bacillus, Beggiatoa, Beijerinckia, Caulobacter, Chlorofrexeus, Chlorogloea, Chromatium, Chromobacterium, Clostridium, Derxia, Ectothiorhodospira, Echerichia, Ferrobacillus, Gamphosphaeria, Haemophilus, Halobacterium, Hyphomicrobium, Lamprocystis, Lampropedia, Leptothrix, Methylobacterium, Methylocystis, Micrococcus, Microcoleus, Microcystis, Moraxella, Mycoplana, Nitrobacter, Nitrococcus, Nocardia, Oceanospirillum, Paracoccus, Photobacterium, Pseudomonas, Rhizobium, Rhodobacter, Rhodospirillum, Sphaerotilus, Spirillum, Spirulina, Streptomyces, Syntrophomonas, Thiobacillus, Thiocapsa, Thiocystis, Thiodictyon, Thiopedia, Thiosphaera, Vibrio, Xanthobacter, Zoogloea, and the like.

The polyhydroxyalkanoate or its copolymer synthesized by fermentation generally has a number average molecular weight, Mn of about 3,000 to 3,000,000. Use of a polyhydroxyalkanoate or its copolymer which has been post-treated by heating or γ-ray irradiation after its synthesis by fermentation to reduce its molecular weight to, for example, about 3,000 to 10,000 is also preferable.

By using a 3-hydroxyalkanoate and/or 4-hydroxyalkanoate (β- or γ-hydroxyalkanoate) polymer having a number average molecular weight of 10,000 to 200,000, and preferably 30,000 to 100,000 for the main component of the resin composition, the period of decrease in the mechanical strength or degradation of the material itself through hydrolysis in a living body may be adjusted within the range of from several months to several years. Consequently, the resin composition can be suitably employed for a flexible medical member to be buried in a living body which should retain its action for a relatively prolonged period of time, for example, a suture, a prosthesis, a coalescence-preventing material, and the like.

When the resin composition is used for a member to be buried in a living body, and the polyhydroxyalkanoate has a number average molecular weight of more than 200,000, the period required for undergoing decrease in the mechanical properties through in vivo hydrolysis would be excessively long such that the buried material would not substantially undergo a sufficient degradation while the material is in its use. On the other hand, when the polyhydroxyalkanoate has a number average molecular weight of less than 10,000, the resin composition would not have a strength required for an implanted member.

Adjustment of the molecular weight can be effected by a post-treatment, for example, a heat treatment or a γ-ray irradiation.

Figure 1:
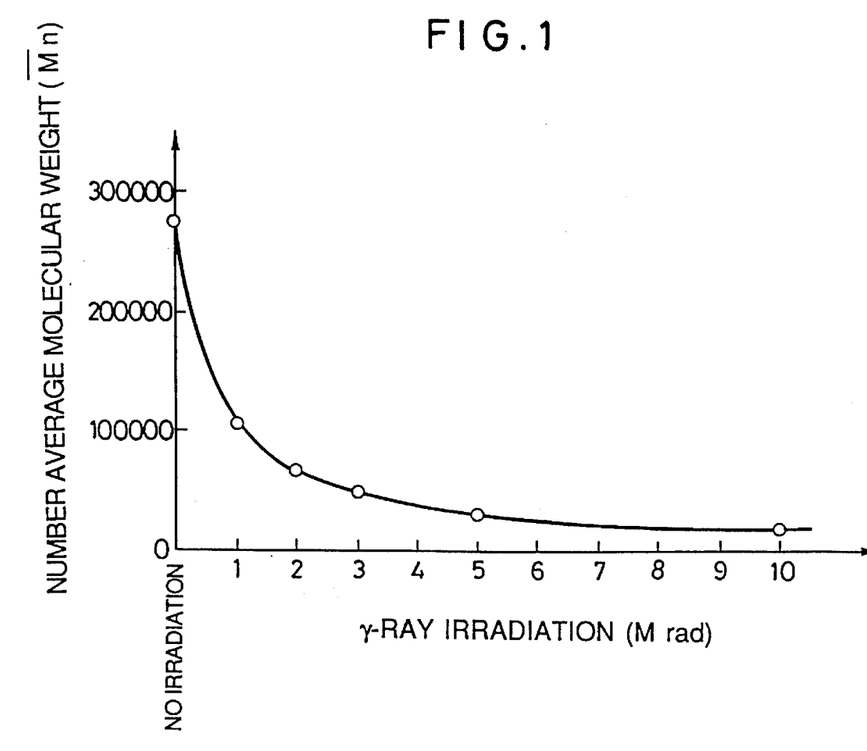
FIG. 1 a diagram showing number average molecular weight of the poly(3-hydroxybutyrate) in relation to dose of the γ-ray irradiated.

A polyhydroxyalkanoate would undergo a decrease in its molecular weight when irradiated with an ionizing radiation, and in particular, γ-ray. In FIG. 1, number average molecular weight of poly(3-hydroxybutyrate), which is a species of poly(β-hydroxyalkanoate)s, is plotted in relation to dose of the γ-ray emitted from cobalt 60. As apparent from the curve of FIG. 1, the number average molecular weight, which is 275,000 before the irradiation of the γ-ray, would decrease in accordance with an increase in the dose of the irradiation to 20,000, which is less than one tenth of the initial molecular weight, by the irradiation of 10 Mrad or the γ-ray. It would be readily appreciated that the molecular weight of the composition can be reduced to any desired degree by controlling the dose of the γ-ray irradiation regardless of the number average molecular weight of the composition before the γ-ray treatment.

Figure 2:
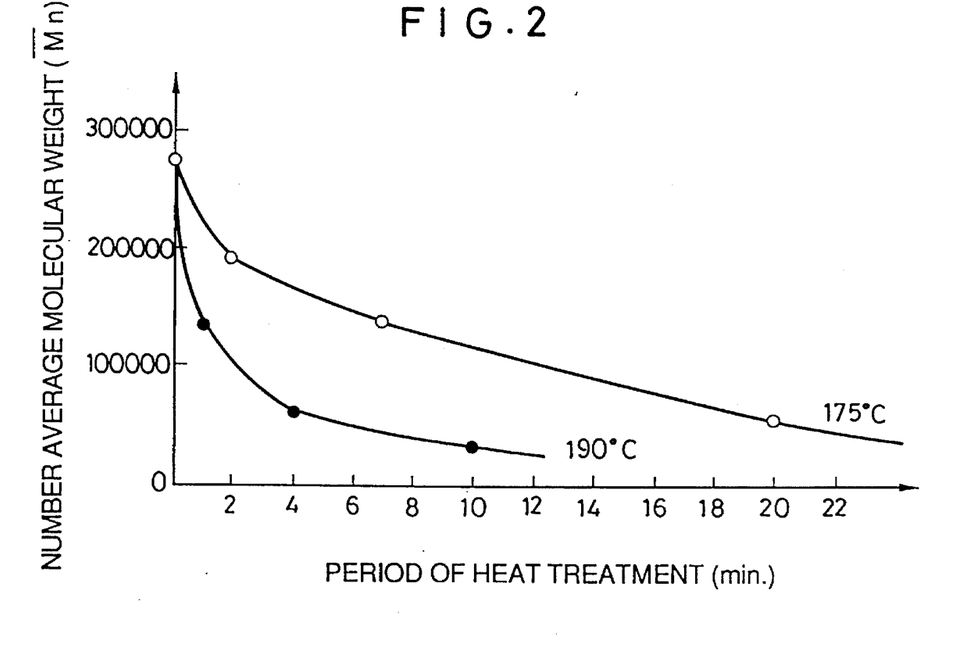
FIG. 2 a diagram showing number average molecular weight of the poly(3-hydroxybutyrate) in relation to period of the heat treatment.

The poly(3-hydroxybutyrate) would also undergo a decrease in its molecular weight when it is heated to a temperature in excess of about 160° C. although its melting point is 180° C. In FIG. 2, number average molecular weight of the poly(3-hydroxybutyrate) is plotted in relation to the period of the heat treatment. According to the curves of FIG. 2, the number average molecular weight would be reduced to about one fourth of its initial value upon heat treating at 175° C. for 20 minutes, and to about one half of its initial value upon treating at 190° C. for 1 minute.

Similar results were obtained for 3-hydroxybutyrate-3-hydroxyvalerate copolymer and 3-hydroxybutyrate-4-hydroxybutyrate copolymer although the results are not depicted.

The molecular weight of the composition can be adjusted to any desired degree by a heat treatment as well as the irradiation with γ-ray. It should be noted, however, that the molecular weight can not be increased by any of such methods. The poly(3- and the poly(4-hydroxyalkanoate) would also undergo a decrease in their molecular weight when they are treated in an acidic solution such as sulfuric acid, hydrochloric acid, hypochlorous acid, or perchloric acid; or in an alkaline solution such as sodium hydroxide or potassium hydroxide, and their number average molecular weight can be similarly reduced to the desired value by adequately selecting the conditions of the treatment to thereby adjust the period required for their biodegradation.

Some experimental examples are hereinafter described.

EXPERIMENT 1

Poly(3-hydroxybutyrate) (number average molecular weight, Mn of 275,000) purchased from Aldrich Corporation in an amount of 0.6 g was fully dissolved in 30 ml of chloroform (guaranteed grade; manufactured by Wako Pharmaceutical K.K.). The resulting solution was cast into a glass Petri dish to obtain a film having a thickness of from 50 to 70 μm after evaporation of the chloroform. The thus obtained film was irradiated with 1 Mrad of γ-ray emitted from cobalt 60. The number average molecular weight was then reduced to 100,000. The number average molecular weight was measured by liquid chromatography using LC-6A manufactured by Simadzu Seisakusho Ltd. having secured thereto a column, Shodex GPC-80M manufactured by Showa Denko K.K. using a differential refractometer for the detector, solvent of chloroform, and a standard of polystyrene.

EXPERIMENT 2

Into 500 ml Sakaguchi flask (shaking flask) was poured a medium comprising 1 g of yeast extract (manufactured by DIFCO corporation), 1 g of polypeptone (manufactured by Nippon Pharmaceutical K.K.), 0.5 g of meat extract (Kyokuto Pharmaceutical Industries K.K.), and 0.5 g of ammonium sulfate (manufactured by Wako Pharmaceutical K.K.) dissolved in 100 ml of distilled water. The medium was inoculated with *Alcaligenes eutrophus* H16 (ATCC 17699), which is a hydrogen bacteria, closed with a cotton plug, and then cultivated at 30° C. for 2 days under shaking. The thus propagated bacteria of 10 Sakaguchi flasks were collected by a centrifugation at 6,000 rpm for 15 minutes. Another medium was prepared by adding 1.0 ml of 20wt/vol % magnesium sulfate, 1.0 ml of the mineral solution shown in Table 1, and 20 g of fructose (Kanto Chemical K.K.) to a phosphate buffer solution, pH 7.5 containing 14.0 ml of 0.5M potassium dihydrogenphosphate and 124.0 ml of 0.25M disodium hydrogenphosphate per 1l buffer solution. The thus prepared medium was poured into a 2.6 l jar fermentor (manufactured by Marubishi Bioengeneering K.K.), and the bacteria which had been collected by the centrifugation were transferred into the jar fermenter. Cultivation was carried out at 30° C. for 48 hours at a stirring blade-rotating rate of 500 rpm and a bubbling rate of 1 ml/min. After completing the cultivation, the propagated bacteria were collected by centrifugation at 6,000 rpm for 15 min. The thus collected bacteria were washed with water and lyophilized. Into 2 l of chloroform was added 11.2 g of the thus lyophilized bacteria, and the suspension was stirred at room temperature for 24 hours to extract the polymer product. The extract-containing solution was filtered to remove insoluble bacteria components, and the filtrate was then dropped into about 10 volumes of n-hexane (first grade; manufactured by Wako Pharmaceutical K.K.) to precipitate the polymer. The thus precipitated polymer was confirmed to be poly(3-hydroxybutyrate) by measuring with $^1$H-NMR (nuclear magnetic resonance spectrometer, EX 90; manufactured by JEOL Ltd.) The polymer product was also evaluated for its number average molecular weight by gel chromatography to be 775,000. Upon irradiation of the polymer product with 10 Mrad of γray emitted from cobalt 60, the number average molecular weight was reduced to 80,000.

TABLE 1

| Composition of the mineral solution (in 1 l of 0.1N HCl) | | | |
|---|---|---|---|
| $CoCl_2$ | 119.0 mg | $NiCl_2.6H_2O$ | 118.0 mg |
| $FeCl_3$ | 9.7 g | $CrCl_3$ | 62.2 mg |
| $CaCl_2$ | 7.8 g | $CuSO_4.5H_2O$ | 156.4 mg |

EXPERIMENT 3

The poly(3-hydroxybutyrate) synthesized in Experiment 2 was heat treated by placing it in an oven at 190° C. for 10 minutes. The resulting polymer had a number average molecular weight of 120,000.

EXPERIMENT 4

The procedure of Example 2 was repeated except that the fructose was replaced with sodium 4-hydroxybutyrate (manufactured by Aldrich Corporation) to produce 1.2 g of 3-hydroxybutyrate-4-hydroxybutyrate copolymer (comprising 20% by mole of 4-hydroxybutyrate unit) having a number average molecular weight of 467,000. The thus produced copolymer product was added to a 100 ml solution comprising 1 volume of aqueous solution of sodium hypochroride (manufactured by Wako Pharmaceutical K.K.) and 1 volume of distilled water, and the suspension was heated to 50° C. for 2 hours. The resulting product had a number average molecular weight of 182,000.

EXPERIMENT 5

The procedure of Example 2 was repeated except that the fructose was replaced with valeric acid (first grade; manufactured by Wako Pharmaceutical K.K.) to produce 3.8 g of 3-hydroxybutyrate-3-hydroxyvalerate copolymer (comprising 63% by mole of 3-hydroxyvalerate unit) having a number average molecular weight of 225,000. The thus produced copolymer product was irradiated with 3 Mrad of γ-ray emitted from cobalt 60. The resulting product had a number average molecular weight of 50,000.

The results of the Experiments are summarized in Table 2.

TABLE 2

| Exp. No. | Polymer structure | MW before treatment | Type of treatment | MW after treatment |
| --- | --- | --- | --- | --- |
| 1 | poly(3-hydroxy butyrate) | 275,000 | 1 Mrad γ-ray | 100,000 |
| 2 | poly(3-hydroxy butyrate) | 775,000 | 10 Mrad γ-ray | 80,000 |
| 3 | poly(3-hydroxy butyrate) | 775,000 | 190° C., 10 min. | 120,000 |
| 4 | 3-hydroxybutyrate-4-hydroxybutyrate copolymer | 467,000 | sodium hypochloride, 50° C., 2 h. | 182,000 |
| 5 | 3-hydroxybutyrate-3-hydroxyvalerate copolymer | 225,000 | 3 Mrad γ-ray | 50,000 |

EXPERIMENT 6

Film pieces of about 50 μm thick with a size of 1×1 cm were prepared from the polymers produced in Experiments 1 to 5 by solvent casting. The film pieces were buried in the back of a rat under its skin. After one year of the burial, the film pieces were retrieved and inspected.

Upon burial for one year, no substantial decrease in mechanical strength of the each film was recognized. Each film, however, had undergone a considerable decrease in its number average molecular weight. The time that would be required for undergoing a substantial decrease in the mechanical strength was estimated from the data of the decrease in the number average molecular weight of the each film. The results are shown in Table 3.

COMPARATIVE EXPERIMENT 7

The poly(3-hydroxybutyrate) synthesized in Experiment 2 which had not been subjected to the γ-ray irradiation was subcutaneously buried in the back of a rat as in the case of Experiment 6. The molecular weight after 1 year burial as well as the estimated time required for undergoing substantial decrease in the mechanical strength are shown in Table 3. The results indicate that, although the material had undergone some decrease in its molecular weight, the time that would be required for deterioration of the mechanical strength is as long as 20 years, and estimated period for complete disappearance (solubilization in water) of the material is as long as about 50 years. The material, therefore, can not be deemed as essentially in vivo biodegradable.

COMPARATIVE EXPERIMENT 8

A polylactic acid film (number average molecular weight, Mn of 100,000; purchased from Polyscience K.K.) was subcutaneously buried in the back of a rat as in the case of Experiment 6. Upon inspection after 1 year burial, the film had undergone a complete degradation to leave no traces. It is estimated that the film had experienced a substantial decrease in its mechanical strength in several days. Degradation of this material is too fast.

COMPARATIVE EXAMPLE 9

The poly(3-hydroxybutyrate) synthesized in Experiment 1 which had not been subjected to the γ-ray irradiation having a number average molecular weight of 275,000 was subcutaneously buried in the back of a rat as in the case of Experiment 6. The molecular weight after 1 year burial as well as the estimated time required for undergoing substantial decrease in the mechanical strength are shown in Table 3. This material would require 5 years for substantial decrease in its mechanical strength, and this period is rather too long in practical point of view. Furthermore, this material would require a period of as long as from fifteen or sixteen years to several decades for its complete disappearance (solubilization in water) to leave no debris, to render the material unusable.

TABLE 3

|  | Molecular weight | | Estimated time |
| --- | --- | --- | --- |
|  | before burial | after burial for 1 year | required for reduction in mechanical strength |
| (Exp. 1) | 100,000 | 70,000 | 1.5 years |
| (Exp. 2) | 80,000 | 68,000 | 1.5 years |
| (Exp. 3) | 120,000 | 97,000 | 3 years |
| (Exp. 4) | 182,000 | 100,000 | 2 years |
| (Exp. 5) | 50,000 | 48,000 | 3 years |
| Comparative Exp. 7 | 775,000 | 563,000 | 20 years |
| Comparative Exp. 8 | 100,000 | not determined | several days |
| Comparative Exp. 9 | 275,000 | 221,000 | 5 years |

EXPERIMENT 10

In 300 ml of chloroform (first grade; manufactured by Wako Pharmaceutical. K.K.) were dissolved 30 g of the γ-ray irradiated poly (3-hydroxybutyrate) (number average molecular weight 100,000) and 9 g of glycerol tributyrate (manufactured by Tokyo Chemical K.K.), and stirred. The solvent was distilled to produce a mixture of the poly(3-hydroxybutyrate) and the glycerol tributyrate. The mixture was cut into pellets using scissors.

The thus produced pellets were charged in a small-sized, small-amount extruder (manufactured by Ohba Works K.K.) to extrude a string-like extrudate from a nozzle having an inner diameter of 0.5 mm at a cylinder temperature of 178° C. and a die temperature of 176° C. The string-shaped extrudate was quenched immediately after the extrusion by using liquid nitrogen. The quenched product was gradually (manually) stretched in a stretching machine at room temperature (about 29° C.) to more than ten folds of its original length until it was almost at break. The resulting product was heat-treated in an oven at a temperature of 60° C. for 3 hours to produce a flexible thread-like product (suture) having an outer diameter of 0.10 mm. The thus produced thread-like product was sterilized with ethylene oxide gas, and attached to Bear stitching needle (round needle, strongly curved, #0) manufactured by Kyowa Clock Industries K.K., to stitch an incision in the back of a rat. The suture was removed after two weeks. No specific problem was noted during its use.

EXPERIMENT 11

The procedure of Experiment 6 was repeated except that the poly(3-hydroxybutyrate) which had not under gone the the γ-ray irradiation (number average molecular weight, 275,000) was used to obtain a thread having an outer diameter of 0.10 mm. The thread was then exposed to 1 Mrad of γ-ray irradiation. The resulting suture was used for stitching an incision at the back of a rat as in the case of Experiment 10. The suture was removed after two weeks. No specific problem was noted during its use. The number average molecular weight after the sterilization was 100,000.

EXPERIMENT 12

A suture having an outer diameter of 0.08 mm was obtained by repeating the procedure of Experiment 6 except that the orientation conditions were somewhat altered. The resulting suture was attached to Bear stitching needle (round needle, strongly curved, #0) to stitch an incision in intestine of an adult crossbred dog (weight, approx. 12 kg). Upon inspection after about one year by incising the abdomen, the incision had been successfully sutured, and the suture was located at its original place.

EXPERIMENT 13

The procedure of Experiment 6 was repeated except that the γ-ray irradiated 3-hydroxybutyrate-3-hydroxyvalerate copolymer prepared in Experiment 5 (number average molecular weight, 50,000) was used to produce a suture. The thus produced suture was attached to a stitching needle to stitch the skin in the back of a rat. No specific problem was noted in the use of the suture.

EXPERIMENT 14

The 3-hydroxybutyrate-4-hydroxybutyrate copolymer after its treatment(number average molecular weight, 182,000) was fabricated into a film of 0.3 mm thick by solvent casting using chloroform. A film piece of 30 mm× 30 mm was cut out of the film, and inserted in abdominal cavity of a rat between the incision in the skin and the intestine for the purpose of coalescence prevention. Upon inspection after one month, the incision had substantially healed, and no coalescence between the incision and the internal organs was recognized. It was also noted that the film had substantially retained its original shape.

EXPERIMENT 15

The procedure of the Experiment 6 was repeated except that the die of the extruder was replaced with a multi-hole die having 6 holes each having a diameter of 0.3 mm to produce a thread-like product having an outer diameter in the range of from 0.01 to 0.03 mm. A 1 g portion of the thread-like product was placed in a test tube having an inner diameter of 0.8 cm, and compressed with a glass rod inserted into the test tube to fabricate a felt. The thus produced felt was placed inside the abdominal cavity of a rat in contact with various organs. No specific problem was noted for one month.

Although Experiments 10 to 15 were carried out under in vivo conditions using animals, for example, rats, no degradation of the material was recognized in the period of up to 1 year. It is, however, conceived that, with the lapse of time, the materials would undergo a decrease in their mechanical strength, and eventually, a complete deterioration to leave no trace.

The resin composition used for the flexible member for medical use of the present invention contains 0.10 to 60% by weight of a lipid compound in addition to the above-described polyhydroxyalkanoate or a copolymer thereof, which is the main component.

Exemplary lipid compounds which may be blended with the polyhydroxyalkanoate in the resin composition of the present invention include monoglycerides, diglycerides, triglycerides, monocarboxylic acid esters, dicarboxylic acid monoesters, dicarboxylic acid diesters, dialcohol monoesters, dialcobol diesters, tricarboxylic acid monoesters, tricarboxylic acid diesters, tricarboxylic acid triesters.

More illustratively, exemplary monoglycerides include glycerol monoacetate, glycerol monopropionate, glycerol monobutyrate, glycerol monocaproate, glycerol monolaurate, glycerol monomyristate, glycerol monopalmitate, glycerol monostearate, etc.;

diglycerides include glycerol diacetate, glycerol dipropionate, glycerol dibutyrate, glycerol dicaproate, glycerol dilaurate, glycerol dimyristate, glycerol dipalmitate, glycerol distearate, etc.; and triglycerides include glycerol triacetate, glycerol tripropionate, glycerol tributyrate, glycerol tricaproate, glycerol trilaurate, glycerol tripalmitate, glycerol trimyristate, glycerol tristearate, etc.

Other carboxylic acid esters include an ester of a carboxylic acid having 2 to 30 carbon atoms with an alkylalcohol having 2 to 30 carbon atoms. More illustratively, exemplary preferred saturated or unsaturated monocarboxylic acid esters include n-amyl acetate, ethyl propionate, methyl caproate, ethyl crotoate, n-butyl oleate, etc;

saturated or unsaturated dicarboxylic acid monoesters include monomethyl cebaciate, mono-n-butyl maleate, monoethyl terephthalate, etc.;

saturated or unsaturated dicarboxylic acid diesters include dimethyl cebaciate, dimethyl terephthalate, di(2-ethylhexyl) phthalate, di-n-octyl phthalate, etc.;

tricarboxylic acid monoesters include monomethyl trimellitate, mono-n-butyl trimellitate, etc.;

tricarboxylic acid diesters include dimethyl trimellitate, dibutyl trimellitate, etc.;

tricarboxylic acid triesters include trimethyl trimellitate, tributyl trimellitate, etc.;

dialcohol monoesters include ethylene glycol monostearate, propylene glycol monostearate, etc; and dialcohol diesters include ethylene glycol distearate, propylene glycol distearate, etc.

The lipid compounds as mentioned above may be either liquid or solid at normal temperatures.

In the resin composition used for the flexible medical member of the present invention, the lipid compound as described above functions as a plasticizing agent or a flexibility-imparting agent for the polyhydroxyalkanoate. The lipid compound, when mixed with the polyhydroxyalkanoate, may also reduce the melting point of the polyhydroxyalkanoate to enable the resin composition to be worked at a lower temperature and prevent unnecessary decomposition of the composition. The workability of the resin composition is thereby improved. In addition, such an inclusion of the lipid composition, which is generally inexpensive, is advantageous in economic point of view.

In the resin composition, the lipid compound may comprise from 0.01 to 60% by weight, and preferably, from 1 to 40% by weight of the composition. The lipid compound of a content of less than 0.01% by weight is insufficient for improving the physical properties of the polyhydroxyalkanoate. The lipid compound of a content in excess of 60% by weight may induce phase separation of the lipid compound to detract from the physical properties of the resulting flexible medical member.

Mixing of the polyhydroxyalkanoate and the lipid compound may be effected by such means as dissolution of the compounds in a suitable solvent such as chloroform, methylene chloride, 1,2-dichloroethane, and dioxane, followed by stirring and evaporation of the solvent; and addition the lipid compound to the polyhydroxyalkanoate using a mixing roll or an extruder under heating.

Such a resin composition which is utilized in the flexible medical member of the present invention is described in detail in Japanese Patent Application No. 2-76585 filed by the applicant of the present invention.

Use of a complex material comprising the above-described resin composition in admixture with another resin is also adequate for fabricating the flexible medical member of the invention.

The resin which may be used for such a mixing is not limited to any particular species, and various conventional resins may be used in accordance with the desired properties. Exemplary preferable resins include polyethylene, polypropylene, polyvinyl chloride, polyvinyl acetate, ionomer, polyacrylic acid, polyacrylate, polymethacrylic acid, polymethacrylate, polyvinyl alcohol, polystyrene, polyvinylidene chloride, polyethylene terephthalate, polybutyrene terephthalate, nylon, polycarbonate, polyethylene glycol, polypropylene glycol, fluororesin, and copolymers thereof.

As mentioned above, such a resin which is mixed with the above-described resin composition may be adequately selected in accordance with the desired properties. For example, the resin composition may be imparted with mechanical durability by an addition of polyethylene terephthalate; and with a surface water repellency by an addition of a fluororesin.

When a complex material comprising the above-described resin composition mixed with such a resin is utilized for the flexible medical member of the invention, the material may generally contain from about 1 to 70% by weight of such a resin, although the content of the resin may not necessary fall within such a range.

In addition to such a resin, the resin composition may optionally include a filler, a die, a pigment, a lubricant, an antioxidant, a stabilizer, and the like.

Preparation of the complex material by the mixing of such a resin with the above-described resin composition may be effected by such means as dissolution of the resins in a suitable solvent such as chloroform, methylene chloride, 1,2-dichloroethane, and dioxane, followed by stirring and evaporation of the solvent; and mixing of the resins using a mixing roll or an extruder under heating.

At least a part of the flexible member for medical use of the present invention is fabricated from the above-described biodegradable resin composition or a complex material comprising a mixture of such a biodegradable resin composition with various resins (which are hereinafter referred to as the biodegradable materials).

The medical member which is fabricated from such a biodegradable material is not limited to any particular type, and the biodegradable material may be used for fabricating any flexible medical member which has been fabricated from a flexible material such as a polyvinyl chloride having added thereto a phthalic acid-based compound as a plasticizing agent, an elastomer, a rubber, or the like.

Furthermore, the configuration of the member fabricated from the biodegradable material is not limited at all, and the medical member may be a cylindrical member including a tube, a bag, a box, a columnar member, a cone-shaped member, a film, a sheet, a thread, a woven or nonwoven fabric, or a molded article of other irregular configurations.

Examples of the medical member which may be fabricated from the above-described biodegradable material include:

blood transfusion system, infusion system, tubings for blood circuits and the like, connecting tubing, connector, manifold, drop cylinder, branched tube, stopcock, and the like;

blood bag, infusion bag, urinary bag, dialysis bag, perintestinal nutrient bag, and other liquid bags;

catheter to be introduced into urinary tract, digestive tract or other body cavities, and balloon catheter;

suture, mesh, patch, pledget, coalescence-preventing film, prosthesis, and other thread, fabric, or sheet-form products; and staple, clip, and other molded articles.

The flexible member for medical use of the present invention has an excellent biodegradability, and therefore, such members are particularly suitable for disposable medical members.

It should be noted that the flexible member for medical use of the present invention does not have to be fabricated solely from the above-described biodegradable material. It is also possible to fabricate some parts of the flexible medical member from such a biodegradable material, and other parts from a conventional resin material. In the case of a balloon catheter, for example, the biodegradable material may be used for fabricating the balloon or the shaft, and other parts may be fabricated from a conventional resin. In the case of a liquid-accommodating bag, the biodegradable material may be used for the body of the bag while other parts including the connecting portions may be fabricated from a conventional resin.

The flexible medical member may also comprise a laminate of the above-described biodegradable material with another conventional resin.

Figure 3:
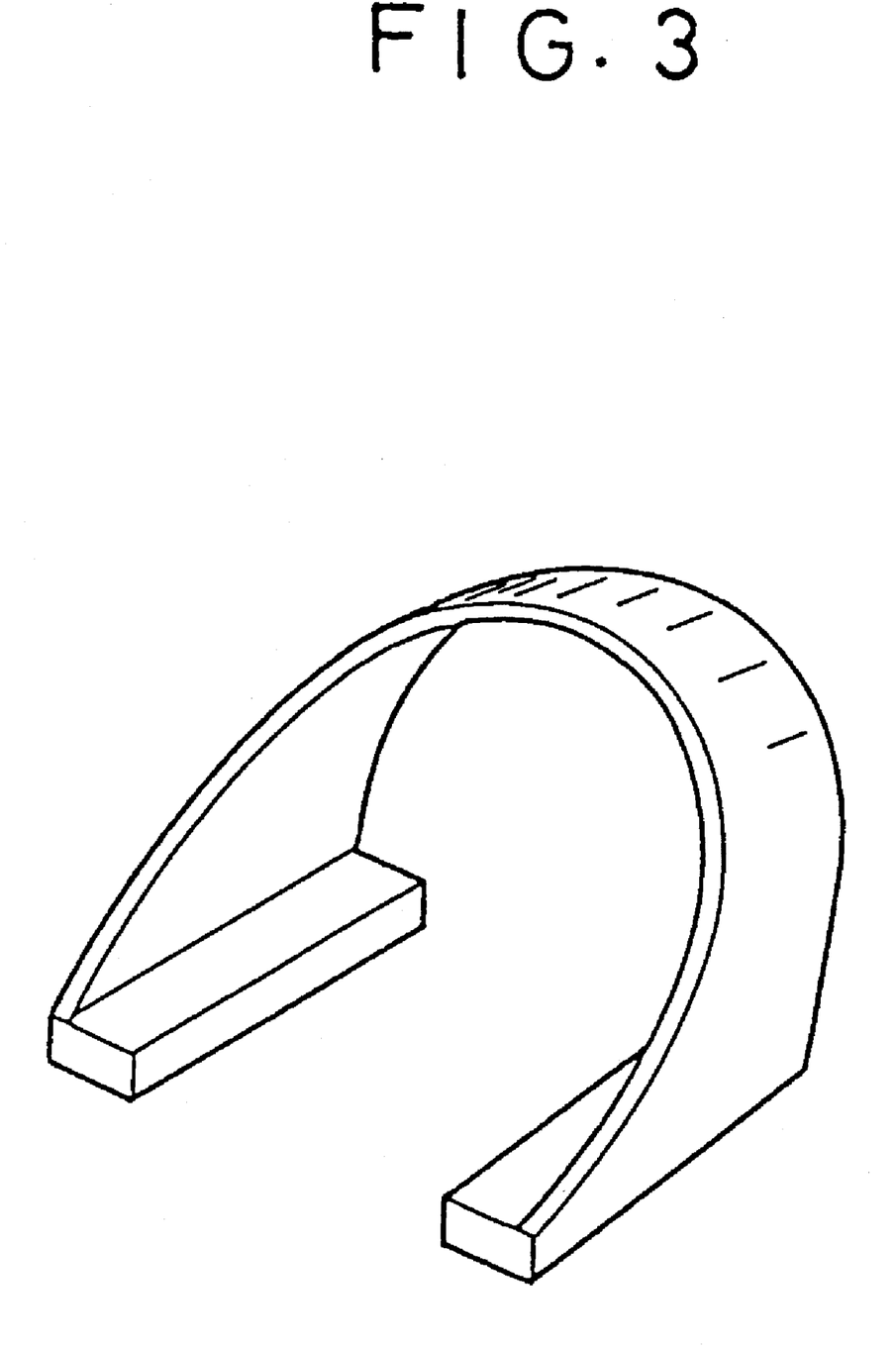
FIG. 3 is a schematic view of an example of a staple which is an embodiment of the flexible medical member according to the present invention.

The biodegradable material used for fabricating the flexible medical member of the present invention has thermoplastic properties. Therefore, the flexible medical member of the invention having a tubular, bag, or other configuration can be fabricated from the biodegradable material by any process used for conventional resins, for example, extrusion molding, injection molding, vacuum molding, press-molding, and the like. An appropriate process may be selected in consideration of the configuration or usage of the resulting medical member as well as installation in which the resulting member is used. For example, a member in the form of a staple as shown in FIG. 3 can be fabricated by such means as injection molding.

The biodegradable material adapted to be used for the flexible medical member of the present invention can be fabricated into a string form by any of the conventional processes employed for extruding a string-like product from conventional thermoplastic resins. For example, the material can be extruded from an extrusion molding machine having a cylinder and a die which has been heated to a temperature 5° to 20° C. higher than the melting point of the biodegradable material to produce a mono-filament or a multi-filament product.

The thus extruded string-like product, which in itself may constitute a flexible medical member of the present invention, may not be fully sufficient in its strength when used as a suture. In such a case, the extrudate may be subsequently stretched for orientation.

Such an orientation by stretching of the thus extruded product may be carried out, for example, by stretching the string-like extrudate in amorphous conditions in its axial direction at a temperature between the glass transition temperature (Tg) and the melting point (Tm) of the material, and subsequently crystallizing the thus stretched product. The thus oriented product will have an increased strength.

The thus produced thread-like product may be fabricated into a braided suture, a woven fabric, a nonwoven fabric, or the like by any conventional process including the one employing a braider or a weaving loom. A suture, a mesh, a patch, or a pledget may be readily fabricated by such a process.

Beside the above-mentioned extrusion, a string-like product may be fabricated from the biodegradable material by a so-called wet spinning process wherein the biodegradable material is dissolved in a solvent such as chloroform and 1,2-dichloroethane, which is capable of dissolving the biodegradable material, to prepare a solution at a concentration of about 2 to 5%, and then extruding the thus prepared solution into a coagulating solvent such as ethanol, methanol and n-hexane with a device having a nozzle such as a syringe to coagulate the material in the string form. Such a process is also preferable.

As mentioned above, the biodegradable material is soluble in such a solvent as chloroform and 1,2-dichloroethane. Therefore, it can be fabricated into a sheet or a film product by such means as casting. The thus formed film may be used, for example, as a coalescence-preventing film.

When the biodegradable material is laminated with another resin to produce a laminate, the biodegradable material may be dissolved in the above-mentioned solvent, and the resulting solution may be dip-coated or roll-coated on the other resin material.

Illustrative methods of fabricating the flexible medical member of the present invention using the above-described resin composition are briefly set forth in the following description.

(1) Fabrication of a Suture

The resin composition used in the present invention has a melting point, and therefore, it can be thermally molded by such means as extrusion molding. For example, such an extrusion molding may be carried out in a small-sized, small-amount extruder (manufactured by Ohba Works K.K.) having mounted thereto a mono-hole die at a temperature 5° to 20° C. higher than the melting point of the material to extrude a mono-filament product. For extruding a multi-filament product, the mono-hole die may be replaced with a multi-hole die. Alternatively, a string-form product may be fabricated by a so-called wet spinning wherein the material of the invention is dissolved in chloroform or dichloromethane to prepare a solution having a concentration of 2 to 5% and the solution is subsequently extruded into a solvent such as n-hexane, methylalcohol or ethylalcohol from a syringe-like nozzle to thereby coagulate the polymer in the string form. If desired, the resulting string-form product may be braided in a braider to produce a braided suture. The string-form product which has been fabricated by either of the above-mentioned processes is in amorphous conditions, and therefore, it may be further oriented by stretching the product in its axial direction at a temperature in the vicinity of or higher than the glass transition temperature (Tg) and retaining the stretched state for a period of time sufficient for promoting a full crystallization. The thus oriented product will be a suture having a sufficient strength.

If desired, the thus produced suture may be further subjected to a surface treatment which is carried out for conventional sutures such as coating with calcium stearate. Also, the suture may be attached to a stitching needle by such means as fitting to prepare a needle-attached suture.

(2) Fabrication of a Mesh and a Pledget

The thread which has been prepared by the above-described suture-fabricating process may be fabricated into a fabric with a weaving loom, or alternatively, fabricated into a Nonwoven fabric by wadding or by using a feltizer. The thus produced woven or nonwoven fabric is subsequently cut into a mesh or a pledget.

(3) Fabrication of a Staple and a Clip

As mentioned above, the material of the present invention has a melting point, and therefore, it can be thermally molded by injection molding to produce a staple or a clip of the desired shape by using a molding temperature which is 10° to 30° C. higher than the melting point of the material.

The flexible member for medical use of the present invention which has been fabricated as described above will be used for the predetermined purposes after sterilization. Sterilization may be carried out by any of various conventional methods such as sterilization in an autoclave, UV sterilization, sterilization with an ionizing radiation, for example, γ-ray or electron beam, gas sterilization using, for example, ethylene oxide, and sterilization using a reagent, for example, an alcohol.

EXAMPLES

The present invention is hereinafter described in further detail by referring to illustrative examples of the flexible member for medical use according to the present invention.

EXAMPLE 1

Poly(3-hydroxybutyrate) (Mw of 670,000; manufactured by Aldrich Corporation) and glycerol trilaurate (manufactured by Tokyo Chemical K.K.) in a weight ratio of 80:20 were dissolved in chloroform, and stirred. The resulting solution was cast to obtain a sheet of 2 mm thick after evaporation of the chloroform.

The resulting sheet was cut with a cutter to produce pellets. The pellets were used for the starting material in the subsequent extrusion molding at a die temperature of 175° C. in an extrusion-molding machine, Plastomil (manufactured by Toyo Precision Machines K.K.) to produce a tubing having an outer diameter of 6 mm and an inner diameter of 4 mm.

No trouble was noted in the molding of the tubing. The resulting tubing was a tough, flexible tubing.

Figure 4:
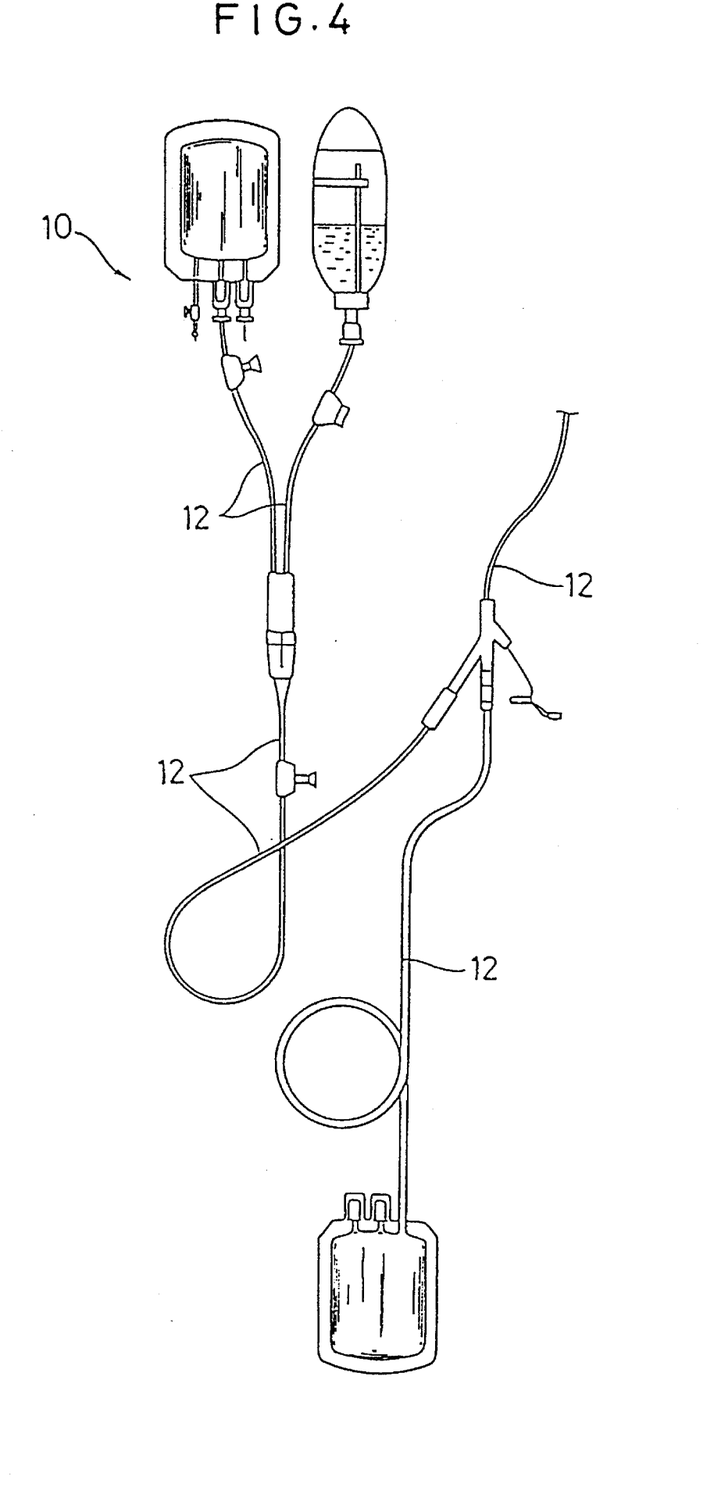
FIG. 4 is a schematic view of an example of an infusion system having employed therein a flexible tube, which is an embodiment of the flexible medical member according to the present invention.

The thus produced flexible tubing was used to assemble an infusion system 10 as shown in FIG. 4. In the infusion system 10, only the flexible tubing 12 was the flexible medical tubing of the present invention, and other member were conventional members. The infusion system was placed in a conventional package bag, and after sealing of the bag, it was sterilized by irradiating 1 Mrad of γ-ray emitted from cobalt 60.

The thus prepared infusion system 10 was used for an infusion of 500 ml of physiological saline (Terumo Physiological Saline; manufactured by Terumo K.K.) at a flow rate of 10 ml/min. No specific problem was noted during the infusion.

The infusion system 10 after its use was buried in soil at Nakai-cho, Ashigarakami-gun, Kanagawa, Japan, and retrieved from the soil burial after six months. The flexible tubing 12 which had been prepared from the flexible medical material of the present invention underwent a complete degradation in soil to leave no original shape.

In contrast, the members of the infusion system comprising conventional materials such as bottle needle, drip cylinder, and clamp fully retained their original shapes after the soil burial.

EXAMPLE 2

The pellets were produced by repeating the procedure of Example 1 except that glycerol triacetate (manufactured by Tokyo Chemical K.K.) was used instead of the glycerol trilaurate, and the mixing ratio of the poly(3-hydroxybutyrate) to the glycerol triacetate was 70:30. The thus produced pellets were used for the starting material in the subsequent extrusion molding, which was carried out by repeating the procedure of Example 1 except that the extrusion was conducted at a die temperature of 160° C. to produce a flexible tubing having an outer diameter of 6 mm and an inner diameter of 4 mm. No trouble was noted in the molding of the tubing. The resulting tubing was a highly flexible, soft tubing.

The thus produced flexible tubing was used to assemble an infusion system similar to the one produced in Example 1, and the infusion system was subjected to an experiment similar to Example 1. No specific problem was noted during its use. When retrieved from the soil burial for six months, the flexible tubing underwent a complete degradation to leave no original shape while other members of the infusion system comprising conventional materials such as bottle needle, drip cylinder, and clamp fully retained their original shapes.

COMPARATIVE EXAMPLE 1

The procedure of Example 1 was repeated except that no glycerol trilaurate was used in the preparation of the tubing. The resulting tubing, which was far from being flexible, became fractured upon assembly of the infusion system, and therefore, an infusion system could not be assembled by using such a tubing.

EXAMPLE 3

Poly(3-hydroxybutyrate) (manufactured by Aldrich Corporation) and glycerol trilaurate (manufactured by Tokyo Chemical K.K.) in a weight ratio of 70:30 were dissolved in chloroform, and stirred. The procedure of Example 1 was repeated to produce pellets.

Figure 5:
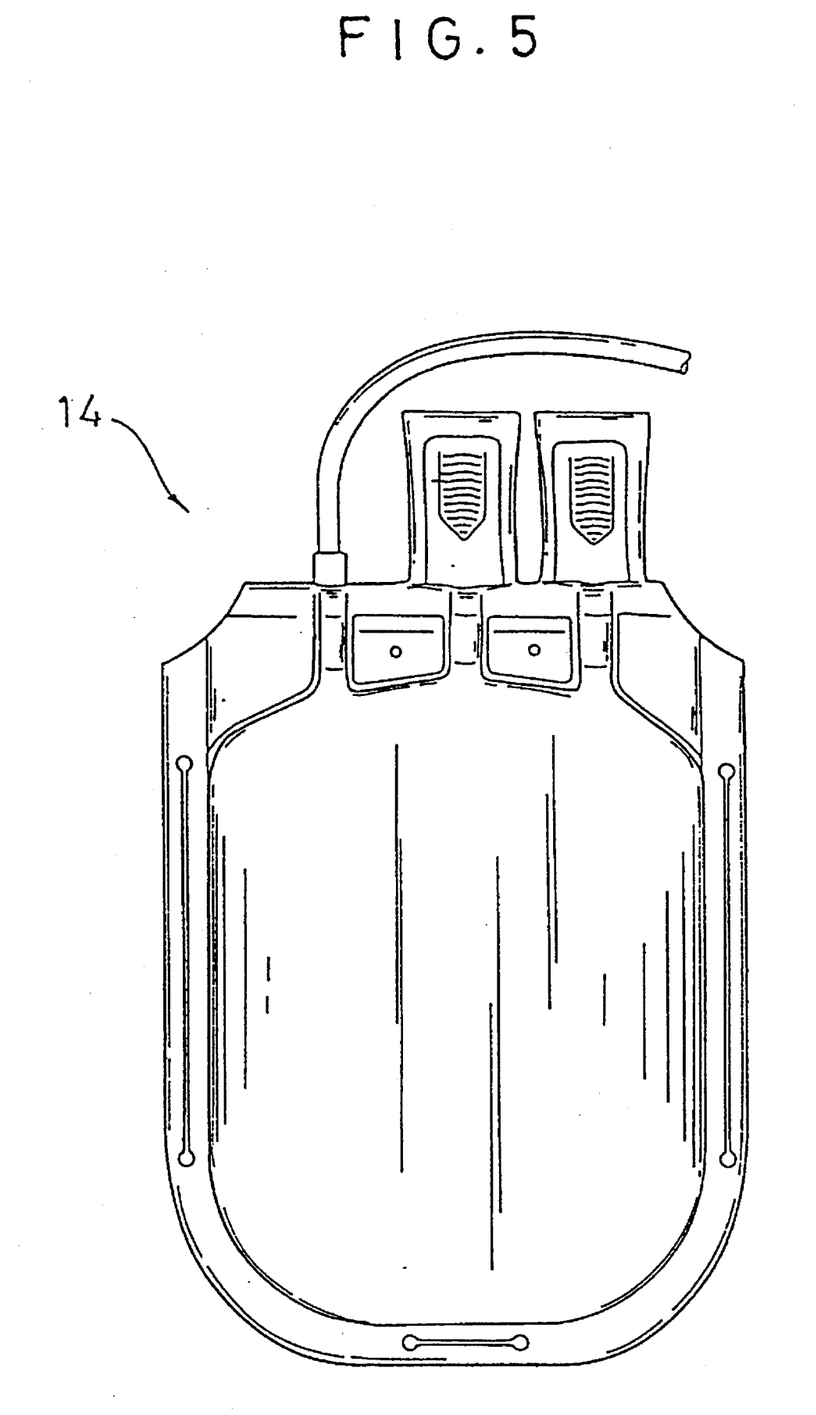
FIG. 5 is a schematic view of an example of a flexible bag which is an embodiment of the flexible medical member according to the present invention.

The pellets were used for the starting material in the subsequent blown-film extrusion at a die temperature of 165° C. in an extrusion-molding machine used in Example 1 to which a blown-film die had been mounted to produce a sheet of 0.4 mm thick. The resulting sheet was heat-sealed to fabricate a flexible bag 14 as shown in FIG. 5. To the thus fabricated bag was connected a tubing produced in Example 2.

No specific trouble was noted in the extrusion. The resulting flexible bag 14 was sufficiently soft.

The flexible bag 14 was filled with 100 ml of physiological saline (Terumo Physiological Saline; manufactured by Terumo K.K.), and then, sterilized in an autoclave at 121° C. for 20 minutes.

The bag was stored for one month at room temperature, and then, visually inspected. Upon inspection, no specific change or inclusion of foreign matter in the content of the bag (physiological saline) was noted. Also, the flexible bag 14 retained its flexibility to an extent that it was capable of enduring a use under normal conditions.

The physiological saline was then discharged from the flexible bag 14, and the thus emptied flexible bag 14 was buried in a soil at Nakai-cho, Ashigarakami-gun, Kanagawa, Japan. When the bag was retrieved from the soil burial of six months, the bag 14 had undergone a complete degradation to leave no original shape.

COMPARATIVE EXAMPLE 2

To 100 parts by weight of straight polyvinyl chloride (S1001, manufactured by Kanegafuchi Chemical Industry Col, Ltd.) was blended 50 parts by weight of dioctyl phthalate and other conventionally employed additives such as an antioxidant. The procedure of Example 3 was then repeated to produce a non-rigid polyvinyl chloride sheet by blown-film extrusion. The resulting non-rigid polyvinyl chloride sheet was subjected to a high-frequency sealing to produce a flexible bag similar to the one shown in FIG. 3.

The thus produced flexible bag was buried in soil for six months in the manner similar to Example 3. No specific change in the appearance was recognized upon visual inspection after retrieval from the soil.

EXAMPLE 4

The procedure of Example 1 was repeated except that a (3-hydroxybutyrate) (3-hydroxyvalerate) copolymer (molar fraction of 3-hydroxybutyrate of 83% Mw of 800,000; manufactured by Aldrich Corporation) was used instead of the poly(3-hydroxybutyrate), and the extrusion was conducted at a die temperature of 150° C. to produce a flexible medical tubing of the present invention.

The thus produced flexible tubing was used to assemble an infusion system similar to the one produced in Example 1, and the infusion system was subjected to an experiment similar to Example 1. No specific problem was noted during its use. When retrieved from the soil burial for six months, the flexible tubing underwent a complete degradation to leave no original shape while other members of the infusion system comprising conventional materials such as bottle needle, drip cylinder, and clamp had retained their original shapes.

EXAMPLE 5

Poly(3-hydroxybutyrate) (Mw=670,000; manufactured by Aldrich Corporation), glycerol tributyrate (manufactured by Tokyo Chemical K.K.), polyethylene terephthalate (Sunpet 3150G; manufactured by Asahi Chemical Industry Co., Ltd.), and an antioxidant (Irganox 1010; manufactured by Chiba-Geigy Corporation) in a weight ratio of 80:20:20:1 were blended, and the blend was directly charged in the extrusion-molding machine used in Example 1 to extrude a bar-shaped extrudate, which was cut into pellets. The thus produced pellets were subjected to a blown-film extrusion at a die temperature of 215° C. to produce a blown-film extruded sheet of 0.4 mm thick.

A flexible bag was produced from the resulting sheet by repeating the procedure of Example 3. No trouble was noted in the above-described process.

The resulting flexible bag had a higher toughness as well as higher resistance to breaking and scratching compared to the one produced in Example 3.

The flexible bag was filled with physiological saline, sterilized in an autoclave, stored for one month at room temperature, and then, visually inspected to find no specific change in the bag or in the content thereof.

The physiological saline was then discharged from the flexible bag, and the thus emptied flexible bag was buried in soil for six months as in the case of Example 1. When the bag was retrieved from the soil burial, it had undergone a substantial degradation to leave tatters. A small amount of powder was also recognized, which was estimated to be the polyethylene terephthalate.

EXAMPLE 6

Poly (3-hydroxybutyrate) (Mw=670,000; manufactured by Aldrich Corporation) and glycerol tributyrate (manufactured by Tokyo Chemical K.K.) in a weight ratio of 80:20 were dissolved in chloroform, and stirred. The resulting solution was cast to obtain a sheet of 2 mm thick after evaporation of the chloroform.

The resulting sheet was cut with a cutter to produce pellets. The pellets were used for the starting material in the subsequent extrusion in a small-sized, small-amount extruder (manufactured by Ohba Works K.K.) to extrude a string-like extrudate from a nozzle having an inner diameter of 0.5 mm at a cylinder temperature of 178° C. and a die temperature of 176° C. The string-shaped extrudate was quenched immediately after the extrusion by using liquid nitrogen.

The fully quenched string-like product was stretched in a stretching machine at room temperature (about 29° C.) to more than ten folds of its original length until it was almost at break.

The resulting product was heat-treated in an oven at a temperature of 60° C. for 3 hours to produce a flexible thread-like product (suture) having an outer diameter of 0.1 mm.

The thus produced thread-like product was sterilized with ethylene oxide gas, and attached to Bear stitching needle (round needle, strongly curved, #0) manufactured by Kyowa Clock Industries K.K., to stitch an incision in the back of a rat. The suture was removed after two weeks. No specific problem was noted during its use.

A remaining length of the suture was buried in soil (at a depth of about 10 cm from the soil surface) at Nakai-cho, Ashigarakami-gun, Kanagawa, Japan, and retrieved from the soil burial after two months. It was observed that the suture had undergone a substantial degradation in soil to scarcely leave its original shape.

EXAMPLE 7

The procedure of the above Example 6 was repeated except that glycerol tricaproate (Tokyo Chemical K.K.) was used instead of the glycerol tributyrate to produce a flexible suture having an outer diameter of 0.1 mm.

An incision in the back of a rat was stitched as in the case of Example 6. No specific problem was recognized in the use of the suture. Upon burial of the suture in soil as in the case of Example 6, the suture underwent a substantial degradation to scarcely leave its original shape.

EXAMPLE 8

The procedure of the above Example 6 was repeated except that glycerol monostearate (Tokyo Chemical K.K.) was used instead of the glycerol tributyrate to produce a flexible suture having an outer diameter of 0.11 mm.

An incision in, the back of a rat was stitched as in the case of Example 6. No specific problem was recognized in the use of the suture. Upon burial of the suture in soil as in the case of Example 6, the suture underwent a substantial degradation to scarcely leave its original shape.

EXAMPLE 9

The procedure of the above Example 6 was repeated except that the die of the extrusion molding machine having a single hole having a diameter of 0.5 mm was replaced with the one having 6 holes each having a diameter of 0.3 mm to produce a thread-like product having an outer diameter of from 0.01 to 0.03 mm after the orientation treatment by stretching.

A 1 g portion of the thread-like product was placed in a test tube having an inner diameter of 0.8 cm, and compressed with a glass rod inserted into the test tube to obtain a felt-like product.

The thus produced felt-like product was placed inside the abdominal cavity of a rat in contact with various organs. No specific problem was noted in the rat after one month.

The remaining felt-like product was buried in soil for two months as in the case of Example 6. The product then underwent a substantial degradation to scarcely leave its original shape.

EXAMPLE 10

Staples shown in FIG. 1 was fabricated with a small-sized, small-amount injection molding machine (manufactured by Arbourg Corporation) using the pellets prepared by repeating the procedure of Example 6.

The thus fabricated staples were used to close an incision in the back skin of a rat. The staples could be used without inducing any specific trouble. The staples were buried in soil as in the case of Example 6. After two months of the burial in soil, the staples underwent a substantial degradation to scarcely leave their original shape.

EXAMPLE 11

The pellets in an amount of 1 g prepared by repeating the procedure of Example 7 were dissolved in 30 ml of chloroform to produce a cast film of 0.6 mm thick on a Petri dish. A piece of the film with a size of 30×30 mm was cut out of the thus produced cast film, and then, sterilized with ethylene oxide gas. The sterilized film was inserted in abdominal cavity of a rat between the incision in the skin and the intestine for the purpose of preventing coalescence of the incision with the internal organs.

Upon inspection of the incision after one month by incising the abdomen of the rat, the incision had substantially healed, and no coalescence between the incision and the internal organs was recognized. It was also noted that the cast film had substantially retained its original shape. The cast film which was not used was buried in soil as in the case of Example 6. In two months, the film had undergone a substantial degradation to scarcely leave its original shape.

INDUSTRIAL UTILITY

The flexible member for medical use of the present invention is fabricated from a predetermined resin composition which has an excellent biodegradability. Consequently, the flexible medical member of the present invention has an excellent biodegradability, and upon burial in soil or disposal in sea after sterilization, it will undergo a degradation in environment in a relatively short period. Therefore, the flexible medical member of the invention would not cause an environmental pollution.

In addition, the flexible member for medical use of the present invention has good workability, high cost performance, sufficient compatibility with ecosystem, and excellent biocompatibility. Therefore, it is suitable for various medical applications including disposable flexible medical members and implants.

We claim:

1. A flexible member for medical use selected from the group consisting of a blood bag, an infusion bag, a dialysis bag and a perintestinal nutrient bag wherein said flexible member comprises a body and at least one fluid port, and said body is fabricated from a resin composition comprising:

at least one member selected from the group consisting of a polyhydroxyalkanoate and a copolymer thereof; and a glyceride, said glyceride comprising 0.01 to 60% by weight of said resin composition.

2. The flexible member for medical use according to claim 1, wherein said polyhydroxyalkanoate is selected from the group consisting of a poly(3-hydroxyalkanoate), a poly(4-hydroxyalkanoate), and a poly(5-hydroxyalkanoate).

3. The flexible member for medical use according to claim 2, wherein said glyceride is selected from the group consisting of monoglyceride, diglyceride and triglyceride.

4. The flexible member for medical use according to claim 3, wherein said glyceride is glycerol tributyrate.

5. The flexible member for medical use according to claim 1, wherein said resin composition further comprises a resin component selected from the group consisting of polyethylene, polypropylene, polyvinyl chloride, polyvinyl acetate, an ionomer, polyacrylic acid, polyacrylate, polymethacrylic acid, polymethacrylate, polyvinyl alcohol, polystyrene, polyvinylidene chloride, polyethylene terephthalate, polybutyrene terephthalate, nylon, polycarbonate, polyethylene glycol, polypropylene glycol, a fluororesin and a copolymer thereof, said resin composition comprising 1 to 70% by weight of said resin component.

6. The flexible member for medical use according to claim 5, wherein resin component is polyethylene terephthalate.

7. A flexible member for medical use according to claim 1, wherein said body and said port comprise said resin composition.

* * * * *

UNITED STATES PATENT AND TRADEMARK OFFICE
CERTIFICATE OF CORRECTION

PATENT NO. : 5,480,394
DATED : January 2, 1996
INVENTOR(S) : Kenji ISHIKAWA

It is certified that error appears in the above-indentified patent and that said Letters Patent is hereby corrected as shown below: On the title page:

In Section [56], kindly insert -- 618107  1/86  Japan --.

In Column 6, line 29, delete "11" and insert --$_{11}$--.

In Column 10, line 25, delete "dialcobol" and insert -- dialcohol --.

In Column 12, line 53, delete "portions" and insert -- portion --.

Signed and Sealed this

Twenty-third Day of July, 1996

Attest:

BRUCE LEHMAN

*Attesting Officer*   *Commissioner of Patents and Trademarks*